US008790638B2

(12) United States Patent
Tankovich et al.

(10) Patent No.: US 8,790,638 B2
(45) Date of Patent: Jul. 29, 2014

(54) COMPOSITIONS OF STEM CELLS AND STEM CELL FACTORS AND METHODS FOR THEIR USE AND MANUFACTURE

(75) Inventors: Nikolai Tankovich, San Diego, CA (US); Alexander Kharazi, San Diego, CA (US); Chih-Min Lin, San Diego, CA (US)

(73) Assignee: Stemedica Cell Technologies, Inc., San Diego, CA (US)

( * ) Notice: Subject to any disclaimer, the term of this patent is extended or adjusted under 35 U.S.C. 154(b) by 302 days.

(21) Appl. No.: 12/573,159

(22) Filed: Oct. 5, 2009

(65) Prior Publication Data

US 2010/0209398 A1     Aug. 19, 2010

Related U.S. Application Data

(60) Provisional application No. 61/149,927, filed on Feb. 4, 2009.

(51) Int. Cl.
*A61K 35/12* (2006.01)

(52) U.S. Cl.
USPC ...................................... 424/93.7

(58) Field of Classification Search
None
See application file for complete search history.

(56) References Cited

U.S. PATENT DOCUMENTS

| | | | |
|---|---|---|---|
| 4,904,259 A | 2/1990 | Itay | |
| 5,053,050 A | 10/1991 | Itay | |
| 5,486,359 A | 1/1996 | Caplan et al. | |
| 5,716,616 A | 2/1998 | Prockop et al. | |
| 6,261,549 B1 | 7/2001 | Fernandez et al. | |
| 6,368,854 B2 * | 4/2002 | Weiss et al. | 435/325 |
| 7,015,037 B1 | 3/2006 | Furcht et al. | |
| 7,097,832 B1 | 8/2006 | Kornowski et al. | |
| 7,635,467 B2 | 12/2009 | Sugaya et al. | |
| 7,635,591 B2 | 12/2009 | Kim et al. | |
| 7,807,458 B2 | 10/2010 | Schiller et al. | |
| 7,968,088 B2 | 6/2011 | Honmou et al. | |
| 2003/0059414 A1 | 3/2003 | Ho et al. | |
| 2005/0170019 A1 | 8/2005 | Roth | |
| 2006/0051334 A1 | 3/2006 | Kornowski et al. | |
| 2006/0057657 A1 | 3/2006 | Baetscher et al. | |
| 2006/0165667 A1 | 7/2006 | Laughlin et al. | |
| 2006/0190044 A1 | 8/2006 | Libbus et al. | |
| 2006/0205071 A1 | 9/2006 | Hasson et al. | |
| 2006/0210544 A1 | 9/2006 | Honmou et al. | |
| 2007/0231306 A1 | 10/2007 | Friedlander et al. | |
| 2008/0219957 A1 | 9/2008 | Lim et al. | |
| 2009/0214484 A1 | 8/2009 | Mironov | |
| 2010/0215714 A1 | 8/2010 | Messina et al. | |
| 2010/0330047 A1 | 12/2010 | Valorani | |
| 2011/0020930 A1 | 1/2011 | Wise et al. | |

OTHER PUBLICATIONS

Li et al, "I ntrastriatal Transplantation of Bone Marrow nonhematopoietic Cells Improves Functional Recovery After Stroke in Adult Mice" Journal of Cerebral Blood Flow and Metabolism, 2000, vol. 20, pp. 1311-1319.*
Wick et al, "Neuroprotection by Hypoxic Preconditioning Requires Sequential Activation of Vascular Endothelial Growth Factor Receptor and Akt" The Journal of Neuroscience, Aug. 2002, vol. 22, No. 15, pp. 6401-6407.*
Xinyang Hu, MD., et al.; The Journal of Thoracic and Cardiovasular Surgery; 2008; 799-808; vol. 135; The American Association for Thoracic Surgery; USA.
Grayson L. Warren, et al.; Journal of Cellular Physiology; Dec. 5, 2005; 331-339; vol. 207; USA.
Chen Jieli, et al.; Journal of the American Heart Association; 2001; 1005-1011; vol. 32; the American Heart Association, Dallas, TX; USA.
Masayuki Kubo, et al.; Translational Physiology; Dec. 2007; H590-H595; vol. 294; AJP—Heart and Circulatory Physiology; USA.
Li Tao-Sheng, et al.; American Journal of Physiology; 2002; H468-H473; vol. 283, No. 2.
Mylotte L.A., et al.; Stem Cells; Feb. 28, 2008; 1325-1336; vol. 26; AlphaMed Press; USA.
Rosova Ivana, et al.; Stem Cells; Aug. 2008; 2173-2182; vol. 8; AlphaMed Press; USA.
Akita Takato, et al.; Laboratory Investigation; 2003; 65-73; vol. 83; Nature Publishing; New York, NY; USA.
Theus M.H., et al.; Experimental Neurology, Apr. 2008, 656-670; vol. 210-2; Epub.; USA.
Basciano, Long Term Culture of Mesenchymal Stem Ceils in Hypoxia Promotes a Genetic Program Maintaining Their Undifferentiated State and Multipotent Status, BMC Cell Biology (2011), vol. 12, p. 1-12.

* cited by examiner

*Primary Examiner* — Allison Ford
(74) *Attorney, Agent, or Firm* — Harris F. Brotman

(57) ABSTRACT

Therapeutic stem cells and methods for their use and manufacture. Stem cells are produced under conditions in which the stem cells are exposed to at least one environmental factor, including decreased oxygen tension. The environmental factors and culture conditions of the invention produce stem cells having an enhanced therapeutic ability and enhanced proliferation in culture. Stem cells of the invention retain their plasticity through a higher number of cell passages relative to know methods of stem cell culture.

3 Claims, 7 Drawing Sheets

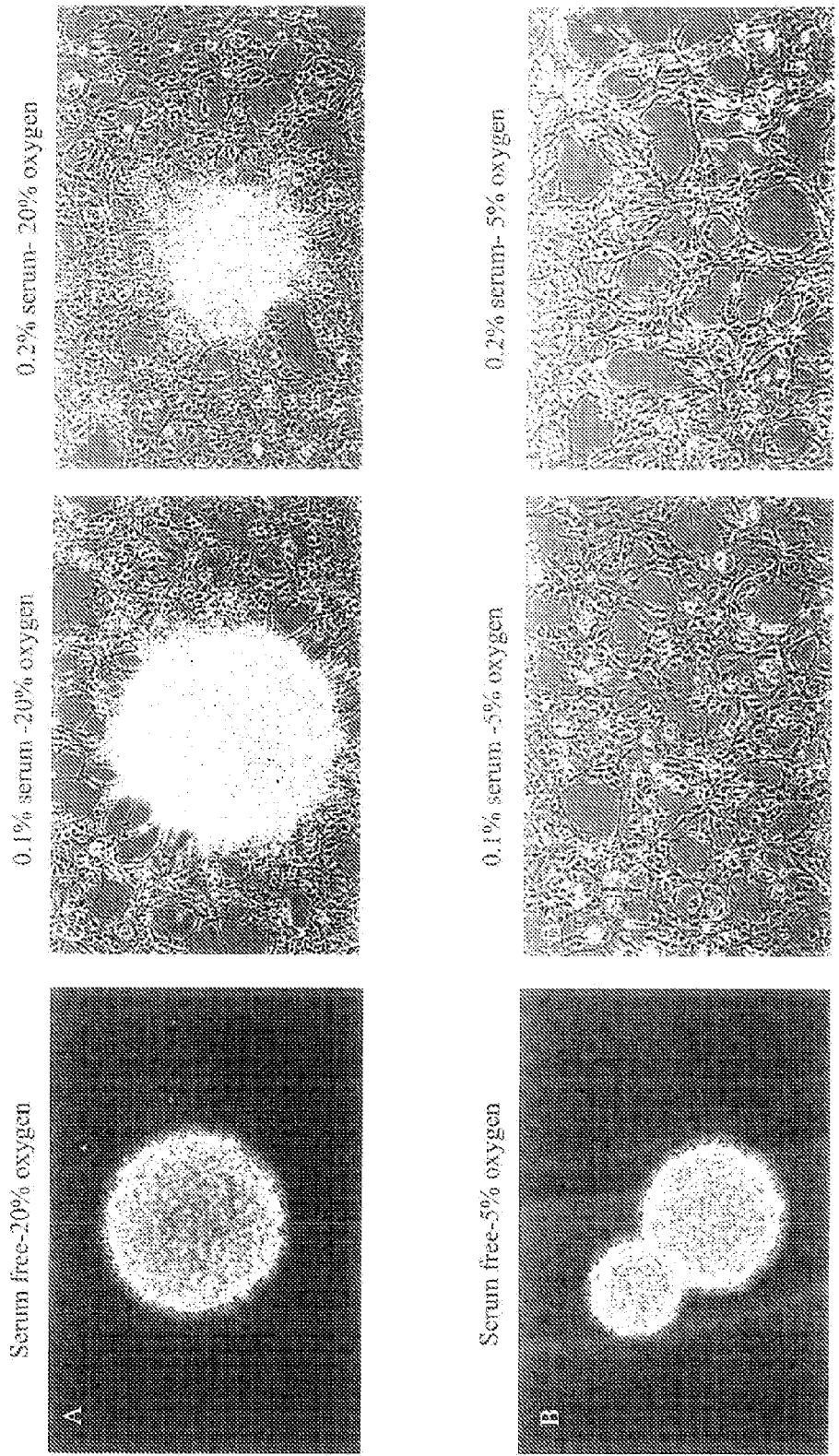

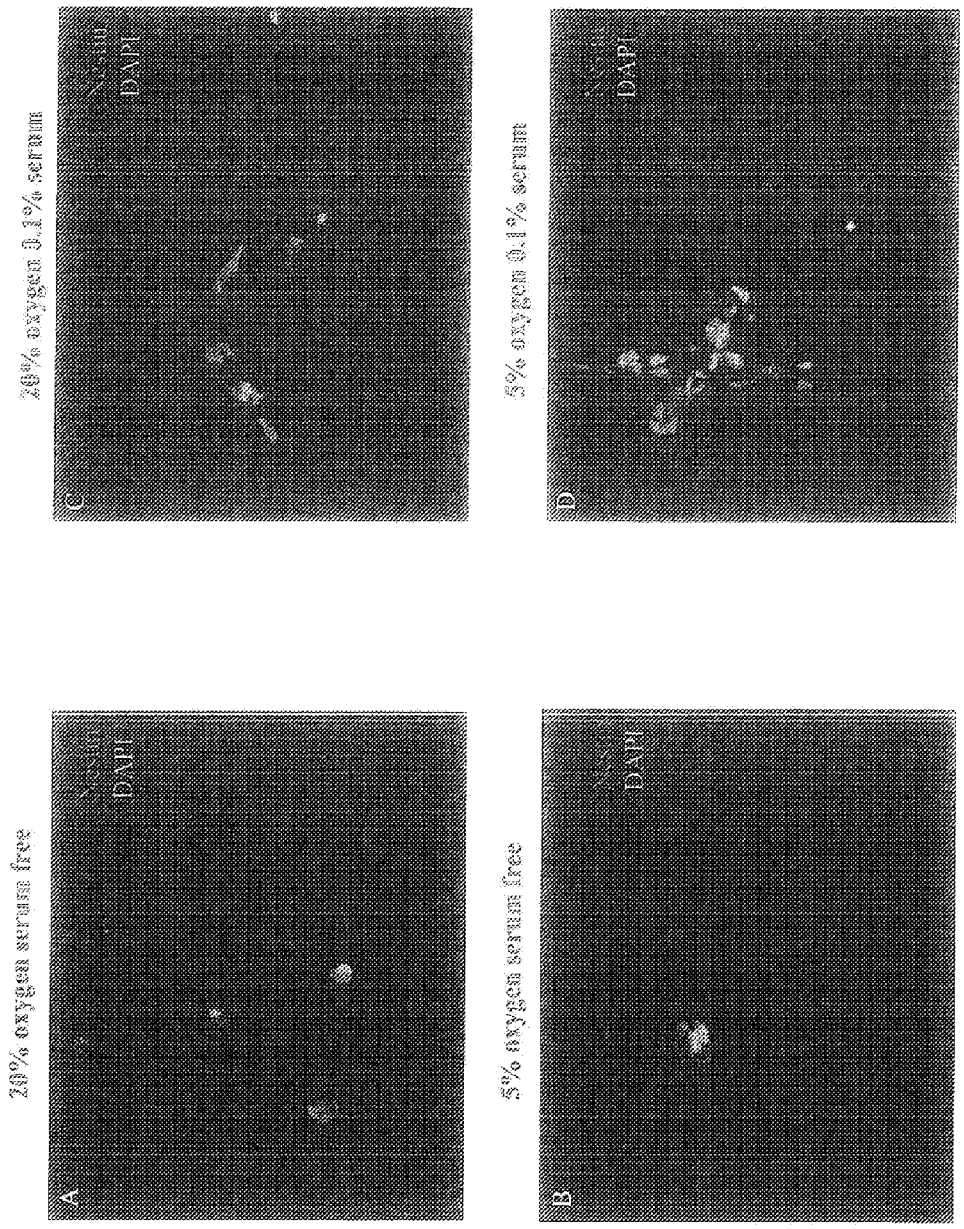

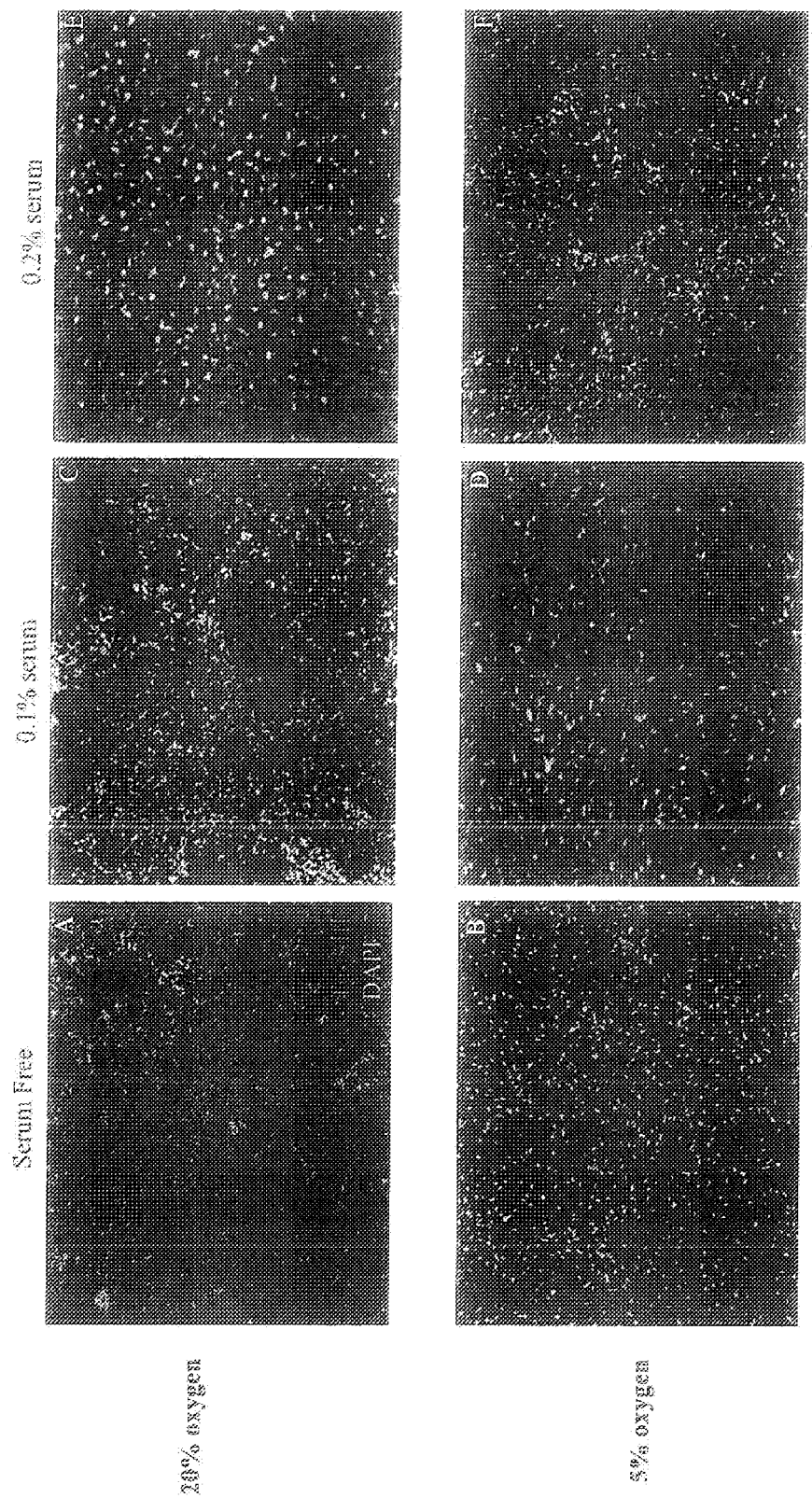
Figure 3. Tubulin-b III (Tu-b III) expression in different culture conditioned cells after in vitro differentiation

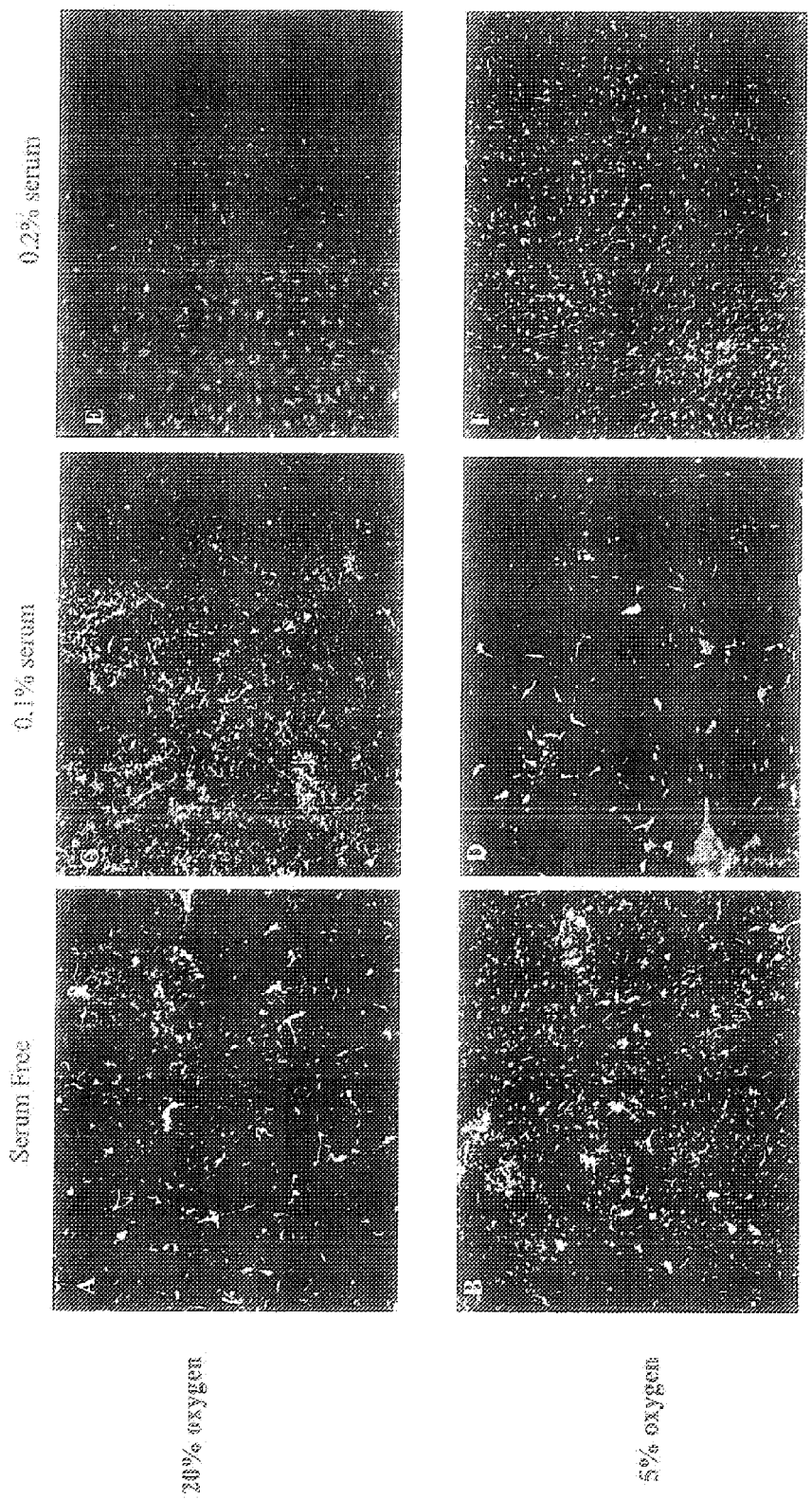

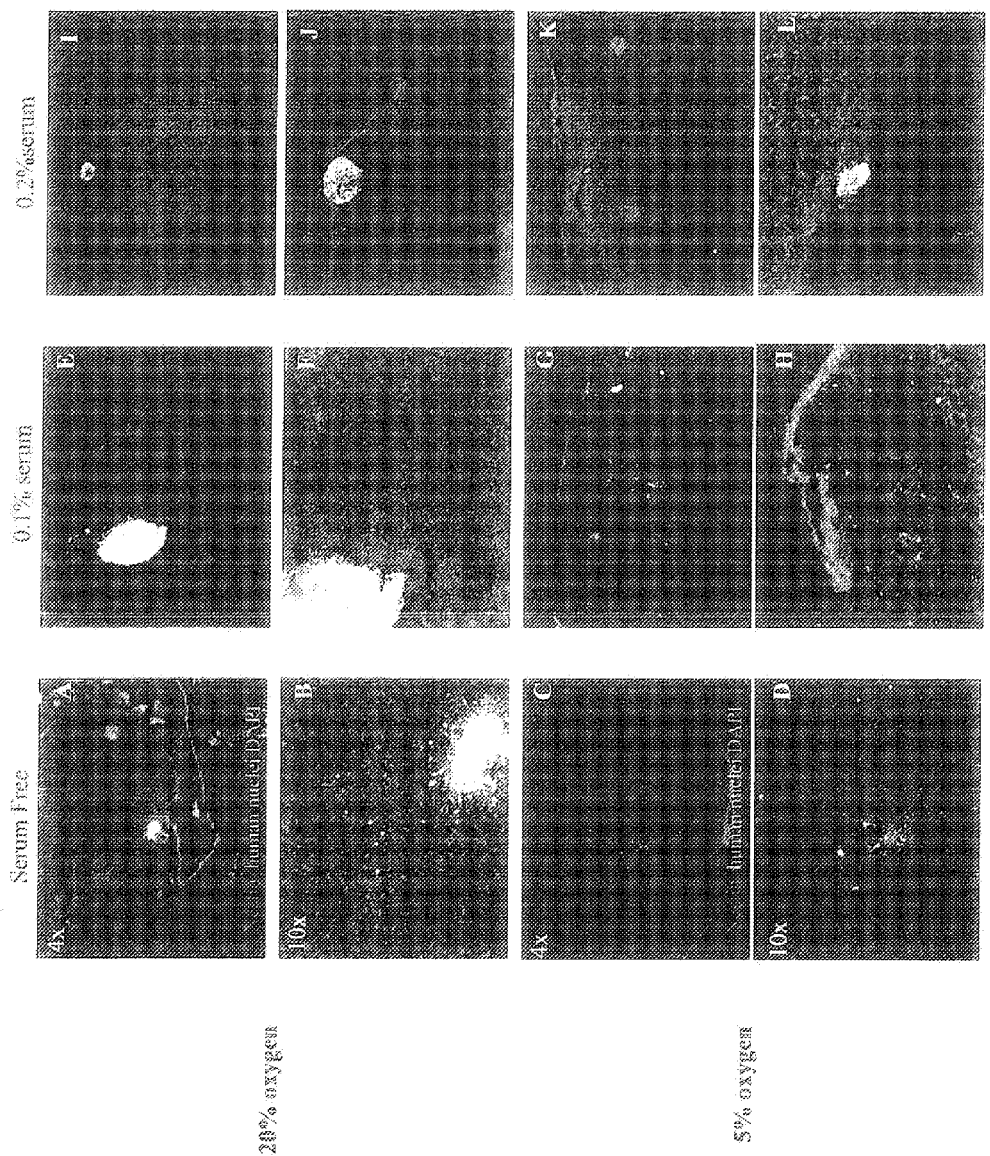
Figure 5. In vivo potency test: different cell migration activities showed in chicken embryonic brain

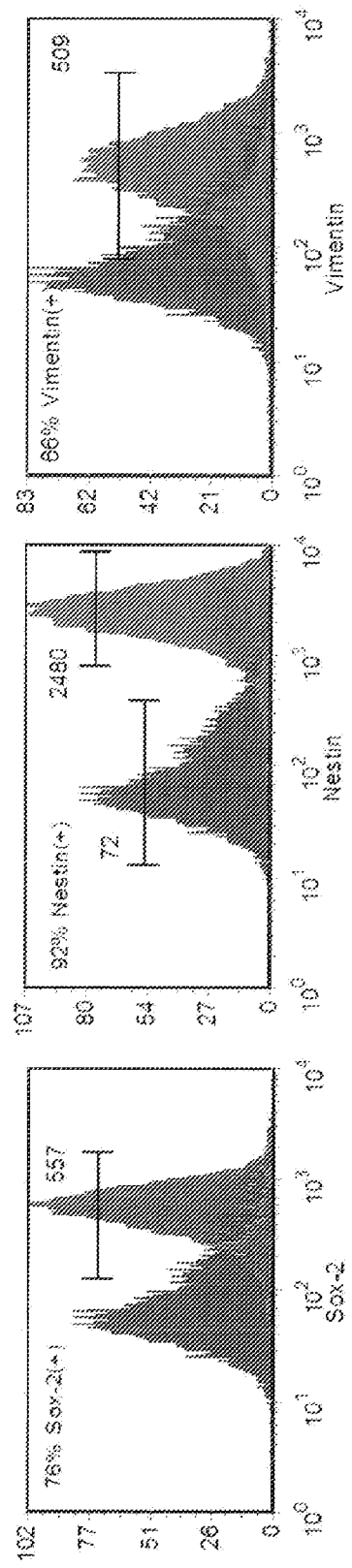
Figure 6. Neural progenitor marker expressions in 0.1% serum and 5% oxygen conditioned cells

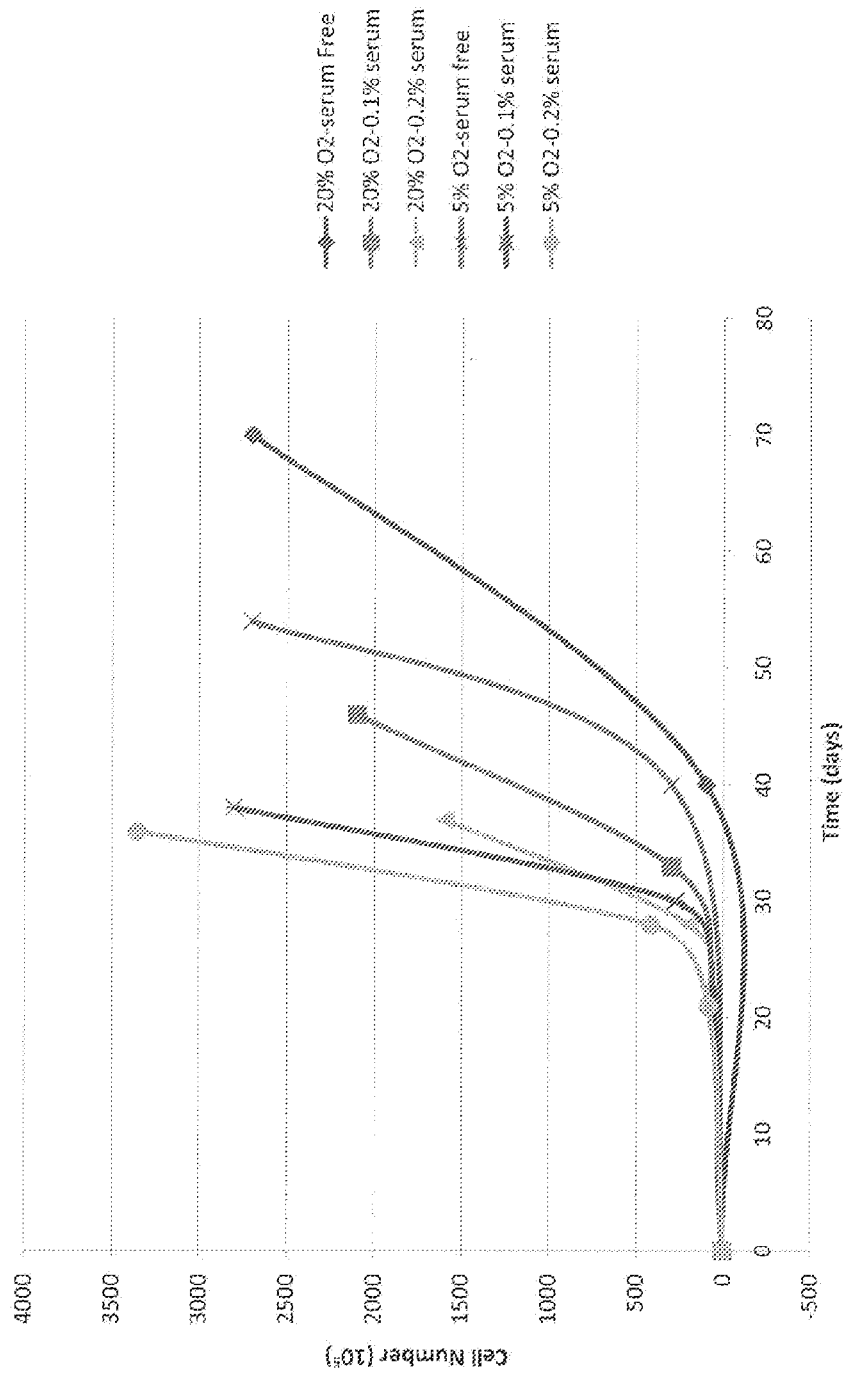

COMPOSITIONS OF STEM CELLS AND STEM CELL FACTORS AND METHODS FOR THEIR USE AND MANUFACTURE

This application claims priority to provisional application Ser. No. 61/149,927 filed Feb. 4,2009 the content of which is incorporated herein by reference in its entirety.

BACKGROUND

Stem cells have shown great promise in treating a wide range of medical conditions. However, stem cell therapy often requires the administration of very large numbers of stem cells which are produced by the in vitro expansion of tissue explants. Because stem cells are present in tissues in relatively small numbers, it is difficult to generate large numbers of stem cells for therapeutic use. This problem is complicated by the loss of differentiation potential that characterizes in vitro stem cell culture. As stem cells spend more time in culture and are encouraged to undergo multiple cell divisions, the differentiation potential of the stem cells diminishes (BMC Cell Biol. 2008 Oct. 28; 9:60; J Cell Physiol. 2005 November; 205(2):194-201). Thus, stem cells must be harvested after only a limited number of cell divisions in order to obtain stem cells having a desired level of differentiation potential.

What is needed in the art therefore is a method for manufacturing stem cells that extends the length of time that stem cells can remain in culture, permits the cells to undergo a greater number of divisions, and allows the stem cells to retain a desired level of stem cell differentiation and therapeutic potential.

SUMMARY OF THE INVENTION

The invention uses environmental factors and cell nutrient conditions to dramatically improve the speed and yield of stem cell manufacture. The invention accomplishes this by increasing cell proliferation and inhibiting the degradation of stem cell potential that characterizes the in vitro expansion of stem cells. Inhibiting the loss of differential potential increases stem cell yield by allowing the stem cells to undergo a greater number of passages while retaining a desired level of potency. The invention accomplishes this while providing the unexpected result of producing a population of stem cells having unique characteristics.

One objective of the invention is to enhance the differentiation potential of an in vitro population of stem cells comprising providing a population of stem cells, culturing the population of stem cells under conditions suitable to expand the population of stem cells, and exposing the population of stem cells to at least one environmental factor, wherein the environmental factor(s) enhances the differentiation potential of the stem cell population relative to a control stem cell population that is not exposed to the environmental factor(s).

A further objective of the invention is to provide stem cells that have a unique biological activity comprising providing stem cells, culturing the stem cells under culture conditions suitable to expand the population of stem cells, and exposing the stem cells to at least one environmental factor, wherein the at least one environmental factor confers upon the stem cells a unique biological activity.

A further objective of the invention is to provide a method for culturing a population of stem cells comprising providing a population of stem cells, culturing the population of stem cells under conditions suitable to expand the population of stem cells, and exposing the stem cells to at least one environmental factor, wherein the environmental factor enhances the proliferation and/or differentiation potential of the stem cell population relative to a control stem cell population that is not exposed to the environmental factor(s).

A further objective of the invention is to provide a method for enhancing the differentiation potential of a population of stem cells comprising providing a population of stem cells, culturing the population of stem cells under conditions suitable to expand the population of stem cells, and exposing the population of stem cells to at least one environmental factor, wherein the stem cells are selected from neural stem cells, mesenchymal stem cells and a combination thereof, and wherein the environmental factor enhances the differentiation potential of the population of stem cells relative to a control neural stem cell population.

Another objective of the invention is to provide a kit for the treatment of a medical condition, the kit comprising a therapeutically effective amount of oxygen modulated neural stem cells, and a therapeutically effective amount of oxygen modulated mesenchymal stem cells.

A further objective of the invention is to provide a kit for treating a medical disorder comprising a therapeutically effective amount of oxygen modulated neural stem cells, and an effective amount of oxygen modulated mesenchymal stem cells.

A further objective of the invention is to provide a method for treating a medical disorder in a patient comprising administering to the patient an effective amount of oxygen modulated neural stem cells, and an effective amount of oxygen modulated mesenchymal stem cells.

A further objective of the invention is to provide a method for treating a medical disorder in a patient comprising administering to the patient an effective amount of stem cell factors derived from oxygen modulated neural stem cells, and an effective amount of stem cell factors derived from oxygen modulated mesenchymal stem cells.

A further objective of the invention is to provide a method for culturing neural stem cells comprising providing neural stem cells, placing the stem cells in contact with culture medium comprising serum, and culturing the stem cells under culture conditions comprising reduced oxygen tension, wherein the stem cells are selected from neural stem cells, mesenchymal stem cells and a combination thereof, and wherein the reduced oxygen tension enhances the differentiation potential of the stem cells.

A further objective of the invention is to provide an in vitro cell culture comprising stem cells and culture medium comprising serum, wherein the culture medium has an oxygen tension that is less than about 5%, and wherein the stem cells are selected from the group consisting of mesenchymal stem cells, ectodermal stem cells and endodermal stem cells.

A further objective of the invention is to provide an in vitro cell culture comprising stem cells and culture medium comprising serum, wherein the stem cells are selected from neural stem cells, mesenchymal stem cells and a combination thereof, and wherein the culture medium has an oxygen tension level that is less than atmospheric oxygen.

A further objective of the invention is to provide a method for increasing the migratory and engraftment potential of a stem cell comprising providing a stem cell, culturing the stem cell under suitable cell culture conditions, and exposing the stem cell to at least one environmental factor, wherein exposing the stem cell to the environmental factor(s) increases the migratory and engraftment potential of the stem cell relative to a control stem cell that has not been exposed to the environmental factor(s).

A further objective of the invention is to provide neural stem cells for use in regenerative cell therapy comprising providing neural stem cells, culturing the neural stem cells under conditions suitable to expand the neural stem cells, and exposing the neural stem cells to an environmental factor that enhances the biological activity of the stem cell relative to control neural stem cells which are not exposed to the environmental factor.

BRIEF DESCRIPTION OF THE DRAWINGS

FIG. 1. Cell morphologies of neural progenitors under various culture conditions. Neural stem cells were collected from the same human fetal brain of eight weeks human embryo. Neural stem cells were divided into six groups. Neural stem cells form neurospheres when they were cultured in serum free conditions. However, neural progenitors become adherent when medium containing serum. A showed the cell morphology in serum free culture medium under 20% oxygen and 5% $CO_2$ culture condition. B showed the cell morphology in serum free culture medium under 5% oxygen and 5% $CO_2$ culture condition. C showed the cell morphology in 0.1% serum culture medium under 20% oxygen and 5% $CO_2$ culture condition. D showed the cell morphology in 0.1% serum culture medium under 5% oxygen and 5% $CO_2$ culture condition. E showed the cell morphology in 0.2% serum culture medium under 20% oxygen and 5% $CO_2$ culture condition. F showed the cell morphology in 0.2% serum culture medium under 5% oxygen and 5% $CO_2$ culture conditions.

FIG. 2 Progenitor marker, nestin expression in different culture conditions. Neural precursor marker, nestin was expressed in all different culture conditioned cells at passage 4. A showed the nestin expression pattern in serum free 20% oxygen conditioned cells. B showed the nestin expression pattern in serum free 5% oxygen conditioned cells. C showed the nestin expression pattern in 0.1% serum 20% oxygen conditioned cells. D showed the nestin expression pattern in serum free 5% oxygen conditioned Adsf.

FIG. 3. Tubulin-β III (Tu--β III) expression in different culture conditioned cells after in vitro differentiation. All conditioned cells were collected and seeded in laminin coated cover slip under no mitogens, 10% serum, and 20% oxygen culture condition for two weeks. Neuron marker, Tu--β III was used for detecting neurons after differentiation. A showed Tu--β III expression pattern under serum free and 20% oxygen condition. B showed Tu--β III expression pattern under serum free and 5% oxygen condition. C showed Tu--β III expression pattern under 0.1% serum and 20% oxygen condition. D showed Tu--β III expression pattern under 0.1% serum and 5% oxygen condition. E showed Tu--β III expression pattern under 0.2% serum and 20% oxygen condition. F showed Tu--β III expression pattern under 0.2% serum and 5% oxygen condition. 0.2% serum under 20% oxygen showed no Tu--β III expression. However, Tu--β III expression was expressed in 0.2% serum under 5% oxygen which suggests oxygen tension rescue cells along neural lineage.

FIG. 4. Glial fibrillary acidic protein (GFAP) expression in different culture conditioned cells after in vitro differentiation. All conditioned cells were collected and seeded in laminin coated cover slip under no mitogens, 10% serum, and 20% oxygen culture condition for two weeks. Neuron marker, GFAP was used for detecting neurons after differentiation. A showed GFAP expression pattern under serum free and 20% oxygen condition. B showed GFAP expression pattern under serum free and 5% oxygen condition. C showed GFAP expression pattern under 0.1% serum and 20% oxygen condition. D showed GFAP expression pattern under 0.1% serum and 5% oxygen condition. E showed GFAP expression pattern under 0.2% serum and 20% oxygen condition. F showed GFAP expression pattern under 0.2% serum and 5% oxygen condition. 0.2% serum under 20% oxygen showed no GFAP expression. However, GFAP expression was expressed in 0.2% serum under 5% oxygen which suggests oxygen tension rescue cells along neural lineage.

FIG. 5. In vivo potency test: different cell migration activities showed in chicken embryonic brain. All conditioned cells were collected for transplantation in chicken embryonic brain for potency assay. $2 \times 10^5$ cells were microinjected into the ventricle of forebrain. Brains were collected after 6 days transplantation for immunohistochemistry. Human specific nuclei and nestin antibodies were used for tracing cell migration after injection in host brain. A and B showed serum free and 20% oxygen cultured cells migrate and incorporate into host brain from ventricle through ventricular zone into striatum. C and D showed serum free and 20% oxygen cultured cells migrate into host brain from ventricle through ventricular zone into striatum. E and F showed 0.1% serum and 20% oxygen cultured cells aggregate between ventricle and ventricular zone and some cells migrate into host brain from ventricle through ventricular zone into striatum. G and H showed 0.1% serum and 5% oxygen cultured cells migrate into host brain. I and J showed 0.2% serum and 20% oxygen cultured cells aggregate in ventricle and no detection of migration. K and L showed 0.2% serum and 5% oxygen cultured cells aggregate between ventricle and some cells migrate into ventricular zone of brain.

FIG. 6. Neural progenitor marker expressions in 0.1% serum and 5% oxygen conditioned cells. Sox 2, nestin and Vimentin were used as progenitor markers for 0.1% serum and 5% oxygen conditioned cells on passage 4.

FIG. 7. Oxygen tension and serum conditional medium increase cell proliferation. NSCs were cultured in 6 different culture conditions. The growth rate showed that 5% oxygen tension increases cell proliferation as well as in serum conditional medium.

DEFINITIONS

The term "stem cell" refers to an undifferentiated cell which has the ability to both self-renew (through mitotic cell division) and undergo differentiation to form a more specialized cell. Stem cells have varying degrees of potency. A precursor cell is but one example of a stem cell.

The term "precursor cell," "tissue precursor cell," or "progenitor cell" refers to an undifferentiated cell that is committed a specific developmental pathway. Precursor cells have limited proliferative ability. "A neural precursor," is one example of a precursor cell that is dedicated to the development of a neuron, glial cell or astrocyte. Another non-limiting example of a progenitor cell is a neuronal progenitor cell which has the ability to differentiate to become a neuronal cell.

The term "neural stem cell" refers to an ectodermal stem cell having the ability to self-renew and differentiate to form a plurality of neural cell phenotypes. As used herein, "neural cell" refers to cells belonging to the neural cell lineage, including neuronal cells (i.e. unipolar, bipolar and multipolar neurons) and glial cells (i.e. oligodendrocytes, Schwann cells, astrocytes, and microglia). "Neural-potent," or "neural-potency," refers to the ability of a stem cell to assume a neural cell phenotype.

"Differentiation" refers to the biological process by which a less specialized cell becomes a more specialized cell type. For example, during embryonic development, pluripotent embryonic stem cells "differentiate" to form multipotent mesenchymal, ectodermal and endodermal stem cells, each of which are limited to a specific developmental pathway (i.e. range of tissues).

"Differentiation potential," "cell potential," "plasticity" and "potential" are used interchangeably herein to refer to the ability of a stem cell to differentiate into one or more specialized cell types.

"Pluripotent" or "pluripotency," refers to a stem cell having the potential to form specialized cells belonging to the mesoderm, endoderm and ectoderm tissue lineages.

The term "multipotent," or "multipotency" refers to the ability of a stem cell to form more than one cell type belonging to a single germ lineage (e.g. the endoderm or ectoderm or mesoderm). For example, a cell which has the ability to form chondrocytes, adipocytes and osteocytes is a multipotent mesenchymal cell.

"Unipotent," or "unipotency," refers to the ability of a progenitor cell to form a specific, terminal cell type. For example, a neuronal progenitor cell is unipotent for the formation of a neuron.

"Mesenchymal cells," are mesodermal germ lineage cells which may or may not be differentiated. The mesenchymal cells of the invention include cells at all stages of differentiation beginning with multipotent mesenchymal stem cells, down to fully differentiated terminal cells.

"Ectodermal cells," are ectodermal germ lineage cells which may or may not be differentiated. The ectodermal cells of the invention include cells at all stages of differentiation beginning with multipotent ectodermal stem cells, down to fully differentiated terminal cells.

"Endodermal cells," are endodermal germ lineage cells which may or may not be differentiated. The endodermal cells of the invention include cells at all stages of differentiation beginning with multipotent endodermal stem cells, down to fully differentiated terminal cells.

As used herein, the term "environmental factor" means an agent, condition, or form of energy that when exposed to a stem cell, enhances the stem cell's proliferation, differentiation potential, in vivo engraftment ability, and/or in vivo migratory ability relative to a control stem cell that is not exposed to such agent, condition, or form of energy. Environmental factors include, but are not limited to, reduced oxygen tension, electromagnetic energy, mechanical energy, metabolic deprivation, barometric variation, exposure to a chemical agent, and combinations thereof.

"Proliferation" refers to an increase in the number of cells in a population by means of mitotic cell division. "Increased proliferation," or "enhanced proliferation" refers to a measurable increase in the proliferation of a stem cell's in response to exposure to an environmental factor(s), relative the proliferation of a control stem cell that is not exposed to such environmental factor(s).

"Retaining stem cell potency," "maintaining stem cell potency," "enhancing differentiation potential," "inhibiting the loss of stem cell differentiation potential," and the like, refer to the ability of an environmental factor(s) to increase, or reduce the loss of, a stem cell's plasticity during in vitro cell culture over multiple cell passages, relative to a control stem cell that is not exposed to such environmental factor(s).

"Enhanced survival" as used herein may refer to a the delay, or decrease in, cell death (either apoptotic or non-apoptotic cell death) that results from exposure of stem cells to an environmental factor(s), relative to control stem cells that are not exposed to such environment factor(s). "Enhanced," when used to refer to a stem cell's proliferation, means any measurable increase in the stem cell's mitotic cell division rate. When used to refer to a stem cell's differentiation potential, "enhanced" means retaining, or inhibiting the loss of, a stem cell's differentiation potential as the stem cell is expanded and passaged in culture.

A stem cell grown under low oxygen conditions as disclosed herein is referred to as an "oxygen modulated stem cell" or "OM-SC." In instances where the oxygen modulated stem cell is a neural stem cell, such stem cells shall be referred to as "oxygen modulated neural stem cells" or "OM-NSC." Oxygen modulated stem cells that are mesenchymal stem cells shall be referred to as "oxygen modulated mesenchymal stem cells" or "OM-MSC."

The terms "prenatal" and "fetal" refer to the period that precedes the birth of a fetus, beginning with the formation of a diploid zygote. Thus, in the context of the invention, tissues and their associated cells derived from a fetus prior to natural birth, or birth by cesarean section, are fetal (i.e. prenatal) tissues. Tissues obtained from mammalian tissue following the birth (e.g. live and still birth) of the mammal are adult tissues and the cells derived therefrom are "adult cells."

The terms "purified" and "isolated" when used to refer to a cell population (e.g. composition of cells) means the cells in the population are essentially free from cells of a different type. A composition of cells is considered "purified," or "substantially purified," if it contains at least about 75%, at least about 80%, at least about 85%, at least about 90%, at least about 95% or at least about 100% of a desired type.

The term "patient," or "subject," refers to animals, including mammals, preferably humans, who are treated with the pharmaceutical compositions or in accordance with the methods described herein.

The term "pharmaceutically acceptable carrier" (or medium), which may be used interchangeably with the term "biologically compatible carrier" (or medium), refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio.

A "central nervous system disorder," or "CNS disorder," refers to a condition or injury that impairs the normal function of the mammalian central nervous system, such as, for example, neurodegenerative disorders, traumatic injuries (to the brain or spinal cord) and CNS dysfunctions. Neurodegenerative CNS disorders are generally associated with a prolonged deterioration of CNS neural tissue including, but not limited to, Alzheimer's disease, Parkinson's disease, multiple sclerosis (MS), Huntington's disease, amyotrophic lateral sclerosis, cerebral palsy, Gaucher's disease, Tay-Sachs disease, Niemann Pick's disease, sphingomyelin lipidoses, and brain tumors. CNS disorders further include traumatic injuries, such as for example, hemorrhagic stroke, ischemic stroke, and mechanical injuries to the brain and spinal cord. The phrase "CNS disorder" further includes dysfunctions such as, for example, depression, epilepsy, and schizophrenia.

The term "spinal cord injury" refers to a condition occurring when a traumatic event damages cells within the spinal cord, or when the nerve tracts that relay signals up and down the spinal cord are severed or otherwise injured. Some of the most common types of spinal cord injury include contusion and compression. Other types of injuries include, but are not limited to lacerations, and central cord syndrome.

The term "ischemia" refers to local anemia due to mechanical obstruction of the blood supply. "Ischemic" refers to a tissue that has been damaged by ischemia.

The term "stroke" refers to a condition wherein the blood flow to the brain stops or is restricted to the point of causing an impairment of neurological function. The term "stroke" includes ischemic stroke, which may be caused by an obstruction that blocks a blood vessel or artery in the brain, and hemorrhagic stroke which may be caused when a blood vessel in the brain ruptures and spills blood into the surrounding tissue.

The term "CNS ischemia," as used herein, is intended to refer to the partial or complete reduction of blood flow to one or more areas of the brain or spinal cord. The ischemia can be global, e.g. a generalized reduction in blood flow due to systemic hypotension, or focal, e.g. due to a disease in one or more cerebral arteries or localized trauma. The ischemia may be the result of stenosis or occlusion of a blood vessel, for example due to a thrombosis, an embolism, or particle.

The term "neuronal damage," or "neuronal injury," as used herein is intended to refer to the damage that occurs to any cell type (e.g. neurons, astrocytes, glia) in the CNS as a result of a CNS disorder or injury. For example, a lack of blood flow results in the death of cells by necrosis and/or apoptosis.

As used herein, a "therapeutically amount" refers to the number of transplanted cells which are required to produce a therapeutic effect for the disorder which is being treated. For example, where the treatment is for Parkinsonism, transplantation of a therapeutically effective amount of cells will typically produce a reduction in the amount and/or severity of the symptoms associated with that disorder, e.g., rigidity, akinesia and gait disorder.

As used herein, "treating a host," or "treatment," includes prophylactic, palliative, and curative intervention in a disease process. Thus, the term "treatment" as used herein, typically refers to therapeutic methods for reducing or eliminating the symptoms of the particular disorder for which treatment is sought. The term "host," as used herein, generally refers to any warm blooded mammal, such as humans, non-human primates, rodents, and the like, which is to be the recipient of the particular treatment. The terms "host," "patient" and "subject" are used interchangeably.

DETAILED DESCRIPTION

In some aspects, the invention relates to the use of a combination of environmental factors and culture conditions to produce stem cells having enhanced proliferation and differentiation characteristics. In very general terms, such embodiments may be practiced by providing a population of stem cells, culturing the population of stem cells in vitro, and exposing the stem cell population to at least one environmental factor to produce a population of stem cells having at least enhanced differentiation, proliferation and therapeutic characteristics. Methods of using the presently disclosed stem cells are also contemplated as embodiments of the invention.

Environmental Factors

Aspects of the invention relate to exposing stem cells to at least one environmental factor.

Environmental factors for use with the invention include, but are not limited to, reduced oxygen tension, electromagnetic energy, mechanical energy, metabolic deprivation, barometric variation, exposure to a chemical agent, and combinations thereof.

In some embodiments of the invention, exposing stem cells to an environmental factor involves exposing the stem cells to reduced oxygen tension. In general terms, this is accomplished by contacting a composition stem cells with an environment that has a low level of ambient oxygen. The phrases "low ambient oxygen conditions," "low oxygen," and "reduced oxygen tension" refer to any oxygen concentration that is less than atmospheric oxygen. Low ambient oxygen conditions generally means any oxygen concentration below about 20%, preferably below about 15%, more preferably below about 5-10%, at sea level. Low oxygen conditions may be kept as close as possible to the normal physiological oxygen conditions in which a particular stem cell would be found in vivo. Thus, in some embodiments, the conditions employed for cells will depend on the regional origin of a particular cell; such conditions are known to the skilled artisan. "Physiologic" oxygen levels are the range of oxygen levels normally found in healthy tissues and organs.

In one embodiment, the low ambient oxygen conditions comprise an ambient oxygen condition of between about 0.25% to about 18% oxygen. In another embodiment, the ambient oxygen conditions comprise an ambient oxygen condition of between about 0.5% to about 15% oxygen. In still another embodiment, the low ambient oxygen conditions comprise an ambient oxygen condition of between about 1% to about 10% oxygen. In further embodiments, the low ambient oxygen conditions comprise an ambient oxygen condition of between about 1.5% to about 6% oxygen. Of course, these are exemplary ranges of ambient oxygen conditions to be used in culture and it should be understood that those of skill in the art will be able to employ oxygen conditions falling in any of these ranges generally or oxygen conditions between any of these ranges that mimics physiological oxygen conditions for the particular cells. Thus, one of skill in the art could set the oxygen culture conditions at 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, or any other oxygen condition between any of these figures.

One aspect of the invention relates to the timing (e.g. stage of cell culture) at which the stem cells are exposed to low oxygen (i.e. reduced oxygen tension) conditions. One skilled in the art will appreciate that the timing of the exposure of the stem cells to reduced oxygen tension will depend on the stem cell characteristics that are desired. Stem cells may be exposed to reduced oxygen tension at any time during the in vitro culture of the stem cells. Stem cells may be exposed to reduced oxygen tension at times including, but not limited to, after collection of the stem cells as a tissue sample, during disaggregation of such tissue sample, during the primary culture of stem cells, during the in vitro expansion of the stem cells (e.g. over multiple cell passages), during priming (e.g. when stem cells are induced to assume a desired biological activity prior to injection into a subject), and combinations thereof.

In some embodiments of the invention, stem cells are exposed to reduced oxygen tension during the in vitro culture of the stem cells. One skilled in the art will appreciate that there are various methods for culturing stem cells under low ambient oxygen conditions (i.e. reduced oxygen tension). For example, suitable processes, reagents and equipment for practicing the invention are disclosed in the following references, which are incorporated herein by reference: U.S. Pat. Nos. 6,759,242; 6,846,641; 6,610,540; J. Cereb. Blood Flow Metab. 2008 Sep. 28(9):1530-42; Stem Cells. 2008 May 26(5):1325-36; Exp Neurol. 2008 April 210(2):656-70; Mol. Cell. Neurosci. (2007), doi:10.1016/j.mcn.2007.04.003; Experimental Neurology 170, 317-325 (2001); and Neurosignals 2006-07, 15:259-265. Although these references disclose particular procedures and reagents, any low oxygen culture condition capable of expanding stem cells according to the invention may be used.

Stem cells can be exposed to low oxygen conditions under any methodology that permits the stem cells to attain an enhanced differentiation potential, proliferation rate, engraftment ability and/or in vivo migratory ability as disclosed herein. Specialized laboratory facilities may have completely enclosed environments in which the oxygen levels are controlled throughout a dedicated, isolated room. In such specialized areas, low oxygen levels can be maintained throughout the isolation, growth and differentiation of cells without interruption. Physiologic or low oxygen culturing conditions also can be maintained by using commercially-available chambers which are flushed with a pre-determined gas mixture (e.g., as available from Billups-Rothenberg, San Diego, Calif.). As an adjunct, medium can be flushed with the same gas mixture prior to cell feeding. In general, it is not possible to maintain physiologic or low oxygen conditions during cell feeding and passaging using these smaller enclosed units, and so, the time for these manipulations should be minimized as much as possible. Any sealed unit can be used for physiologic oxygen or low oxygen level culturing provided that adequate humidification, temperature, and carbon dioxide are provided.

In addition to oxygen, the other gases for culture typically are about 5% carbon dioxide and the remainder is nitrogen, but optionally may contain varying amounts of nitric oxide (starting as low as 3 ppm), carbon monoxide and other gases, both inert and biologically active. Carbon dioxide concentrations typically range around 5% as noted above, but may vary between 2-10%. Both nitric oxide and carbon monoxide are typically administered in very small amounts (i.e. in the ppm range), determined empirically or from the literature.

One aspect of the invention relates to the length of time that the stem cells are exposed to reduced oxygen tension. Under the invention, stem cells may be exposed to reduced oxygen tension for any amount of time that enhances the proliferation and differentiation of the stem cells as disclosed herein. This may be 1 or more hours, 3 or more hours, 6 or more hours, 12 or more hours, or the time may be continuous (e.g. the entire time that the stem cells are cultured in vitro). The temperature during the culture is typically reflective of core body temperature, or about 37.degree. C., but may vary between about 32 degrees centigrade and about 40 degrees centigrade.

Stem Cells and Culture Conditions

The invention may be used to expand any stem cell (or combination of stem cells) that is capable of being enhanced under the method of the invention. Suitable stem cells for use with the invention include, but are not limited to, pluripotent embryonic stem cells, mesenchymal cells, ectodermal cells, endodermal cells, and combinations thereof.

In some embodiments, the invention is practiced with ectodermal cells. Ectodermal cells for use with the invention include, but are not limited to, multipotent cells derived from the embryonic ectoderm germ layer. Suitable methods for deriving such embryonic ectodermal cells are readily available to one of ordinary skill in the art.

In some aspects of the invention, the ectodermal cells for use with the invention are neural stem cells. Neural stem cells have the ability to self-renew and differentiate to assume a plurality of different neural cell phenotypes. Neural stem cells for use with the invention may be derived from a variety of tissue compartments. In some embodiments, the neural stem cells are derived from nervous tissue. Suitable neural tissue for providing neural stem cells includes (i) the peripheral nervous system, such as for example, the nasal epithelium, pigmented epithelium, non-pigmented epithelium, and ciliary body, (ii) the spinal cord, (iii) all the regions of the brain, including but not limited to, the forebrain, basal forebrain (cholenergic neurons), cerebellum, telencephalon, mesencephalon, hippocampus, olfactory bulb, cortex (e.g., motor or somatosensory cortex), striatum, ventral mesencephalon (cells of the substantia nigra), and the locus ceruleus (neuroadrenaline cells of the central nervous system), and (iv) combinations thereof.

Instructions for deriving neural stem cells from nervous tissue, and culture conditions for expanding such neural stem cells, are readily available in the art as shown by the following publications which are incorporated herein by reference: U.S. Pat. Nos. 5,750,376, 6,497,872, and 6,777,233; 5,196,315; 5,766,948, 5,968,829; 6,468,794, 6,638,763, 6,680,198, 6,767,738, 6,852,532, 6,897,061, 7,037,719; U.S. Patent Publication Nos. 20050112109, 20040048373, 20020039789, 20020039789, 20030095956, 20050118143, 20060148083, 20050074880, 20020086422, 20040253719, 20050003531, 20050125848, 20050142569, 20060099192 and 20060134280.

Neural stem cells for expansion under the methods disclosed herein may also be derived from non-neural (e.g. non-ectodermal) tissue sources. For example, neural stem cells may be derived from mesenchymal stem cells. In some embodiments, this source of mesenchymal cells is the bone marrow. Such cells, in their undifferentiated state, assume a neural phenotype under in vitro conditions, or when introduced to the neural tissue of an animal. Amniotic fluid is another source of cells which can be differentiated into neural precursors. Instructions for deriving neural-potent bone marrow stem cells for use with the invention may be obtained from the following publications, which are incorporated by reference: U.S. Pat. Nos. 6,673,606 and 7,015,037; U.S. Patent Publication Nos. 20020164794, 20030003090, 20030039639, 20030059414, 20030203484, 20040151701, 20040208858, 20050282276, 20050249708, 20060105457, 20060177928; and Mareschi et al. Exp Hematol. 2006 November; 34(11):1563-72. In other embodiments, neural-potent mesenchymal cells are derived from umbilical cord blood. Suitable umbilical cord-derived cells, and their methods of isolation, are disclosed in U.S. Patent Publication Nos. 20020028510, 20050249708, 20040115804, 20050142118 and 20050074435, the disclosures of which are incorporated by reference. Neural-potent mesenchymal cells may also be derived from the scalp (i.e. skin) (see e.g. U.S. Patent Publication Nos. 20030003574, 20040253718 and 20040033597; and Shih et al. Stem Cells 2005 August; 23(7) 1012-1020), the peripheral blood (see e.g. U.S. Patent Publication Nos. 20040136973 and 20050221483), the placenta (see e.g. U.S. Patent Publication Nos. 20050089513 and 20060030039) and the amniotic layer (see e.g. U.S. Patent Publication No. 20030044977).

The neural stem cells for use with the inventive method may be made using purified or non-purified cells, as well as combinations of purified and non-purified cells. Non-purified compositions of neural stem cells may be obtained in a number of ways. In some embodiments, the neural stem cell composition is made by combining separate, purified (i.e. isolated) neural stem cell populations. In other embodiments, the neural stem cell composition is obtained by culturing a mixed population of cells, such as a primary culture obtained from a tissue explant and expanded cell populations obtained therefrom. In still other embodiments, a non-purified composition of neural stem cells is obtained by combining one or more purified cell compositions, with a composition of mixed cell types such as a primary cell culture. Typically, primary cell cultures contain a mixture of cells as a variety of cells are able to grow in culture after being collected from an animal. Thus, primary cultures generally contain a combination of the different cell types which are able to proliferate in vivo. These cell types may have varying phenotypes (e.g. cellular markers) and varying levels of differentiation.

When the method is practiced using a primary culture of neural stem cells, the method generally involves the removal of a nervous tissue from an animal, disaggregation of the neural cells within the sample, and expansion of the cells in a suitable media under appropriate in vitro conditions. In general, three types of cultures can be produced, enriched either in neurons, astrocytes, or oligodendrocytes. Methods for producing primary cultures of neural stem cells are widely available in the art. One such method is disclosed in U.S. Pat. No. 5,753,491, which describes the preparation of a neural stem cell composition from fetal neural tissue. In general, this process involves the collection of fetal brain tissue from fetuses between about 7-11 weeks of gestational age. Following extraction, brain tissue is disassociated to produce a cell suspension which is subsequently plated on culture dishes and expanded under suitable conditions. Although the preparation of human fetal neural tissue is specifically called out here, one skilled in the art will appreciate that fetal neural stem cells may also be derived from both human and non-human post-natal nervous tissue. The teachings of U.S. Pat. No. 5,753,491, and all other publications referred to in this publication are incorporated by reference in their entirety.

Other methods suitable for producing a primary culture of neural cells are readily available in the art. The following publications, which are incorporated by reference, provide the teachings necessary to enable one skilled in the art to prepare a primary culture of neural stem cells for use with the invention: U.S. Pat. Nos. 5,750,376, 6,497,872, and 6,777,233; U.S. Patent Publication Nos. 20050112109, 20040048373, 20020039789, 20020039789, 20030095956, 20050118143, 20060148083, and 20050074880; Isolation, Characterization and Use of Stem Cells from the CNS, 18 Ann. Rev. Neurosci. 159-92 (1995); M. Marvin & R. McKay, Multipotential Stem Cells in the Vertebrate CNS, 3 Semin. Cell. Biol. 401-11 (1992); R. P. Skoff, The Lineages of Neuroglial Cells, 2 The Neuroscientist 335-44 (1996). A. A. Davis & S. Temple, A Self-Renewing Multipotential Stem Cell in Embryonic Rat Cerebral Cortex, 362 Nature 363-72 (1994); A. G. Gritti et al., Multipotential Stem Cells from the Adult Mouse Brain Proliferate and Self-Renew in Response to Basic Fibroblast Growth Factor, 16 J. Neurosci. 1091-1100 (1996); B. A. Reynolds et al., A Multipotent EGF-Responsive Striatal Embryonic Progenitor Cell Produces Neurons and Astrocytes, 12 J. Neurosci. 4565-74 (1992); B. A. Reynolds & S. Weiss, Clonal and Population Analyses Demonstrate that an EGF-Responsive Mammalian Embryonic CNS Precursor is a Stem Cell, 175 Developmental Biol. 1-13 (1996); Cattaneo et al., Mol. Brain. Res., 42, pp. 161-66 (1996); and B. P. Williams et al., The Generation of Neurons and Oligodendrocytes from a Common Precursor Cell, 7 Neuron 685-93 (1991).

Although fetal neural stem cell compositions are called out above, the inventive method may also be practiced with compositions derived from adult neural tissue. Such adult neural stem cells, and methods of deriving them, are taught in the following publications, the disclosures of which are incorporated by reference: U.S. Pat. Nos. 5,356,807, 5,851,832, 6,638,763 and 6,812,027; and U.S. Patent Publication Nos. 20030049234, 20030095956, 20030118566, 20040253719, 20050112109 and 20050118143.

In addition to the use of primary cultures of neural stem cells, the method of the invention further contemplates compositions of purified neural stem cells. In the context of the invention, a cell composition is "purified," or "isolated," if the cells in the composition are essentially free from cells of a different type. A composition of cells is considered "purified," or "substantially purified," if it contains at least about 75%, at least about 80%, at least about 85%, at least about 90%, at least about 95% or at least about 100% of a desired cell type. Neural stem cells for use with the invention may be purified according to methods well known in the art, such as for example, FACS, magnetic sorting, serial passaging, cloning, and affinity chromatography. Such neural stem cells may be purified from a tissue explant or a mixed population of cells grown in culture. Suitable purified cells for practicing the invention, and the methods for making them, are disclosed in the following publications, the disclosures of which are incorporated by reference: U.S. Pat. Nos. 5,196,315, 5,766,948, 5,968,829, 6,468,794, 6,638,763, 6,680,198, 6,767,738, 6,852,532, 6,897,061 and 7,037,719; and U.S. Patent Publication Nos. 20020086422, 20040253719, 20050003531, 20050125848, 20050142569 and 20060099192.

Neural stem cells for use with the invention may also be derived from neural-potent bone marrow mesenchymal stem cells. Such cells, in their undifferentiated state, assume a neural phenotype under suitable in vitro conditions. Amniotic fluid is another source of mesenchymal stem cells which can be trans-differentiated to neural precursors for use with the invention. Instructions for deriving neural-potent bone marrow stem cells for use with the invention are provided by the following publications which are incorporated by reference: U.S. Pat. Nos. 6,673,606 and 7,015,037; U.S. Patent Publication Nos. 20020164794, 20030003090, 20030039639, 20030059414, 20030203484, 20040151701, 20040208858, 20050282276, 20050249708, 20060105457, 20060177928; and Mareschi et al. Exp Hematol. 2006 November; 34(11): 1563-72.

Neural-potent mesenchymal cells for use with the invention are may be derived from umbilical cord blood. Such umbilical cord-derived cells, and their methods of isolation, are disclosed in U.S. Patent Publication Nos. 20020028510, 20050249708, 20040115804, 20050142118 and 20050074435, the disclosures of which are incorporated by reference. Neural-potent mesenchymal cells may also be derived from the skin (see e.g. U.S. Patent Publication Nos. 20030003574, 20040253718 and 20040033597; and Shih et al. Stem Cells 2005 August; 23(7) 1012-1020), the peripheral blood (see e.g. U.S. Patent Publication Nos. 20040136973 and 20050221483), the placenta (see e.g. U.S. Patent Publication Nos. 20050089513 and 20060030039) and the amniotic layer (see e.g. U.S. Patent Publication No. 20030044977). The disclosures of these references are incorporated herein by reference.

Neural stem cells for use with the invention may be derived from human heterologous sources including fetal tissue following elective abortion, or from a post-natal, juvenile or adult organ donor. Autologous neural tissue can be obtained by biopsy, or from patients undergoing neurosurgery in which neural tissue is removed, for example, during epilepsy surgery, temporal lobectomies and hippocampalectomies. Neural stem cells have been isolated from a variety of adult CNS ventricular regions, including the frontal lobe, conus medullaris, thoracic spinal cord, brain stem, and hypothalamus, and proliferated in vitro using the methods detailed herein. In each of these cases, the neural stem cell exhibits self-maintenance and generates a large number of progeny which include neurons, astrocytes and oligodendrocytes.

The invention may also be used to expand a purified population of neural stem cells. Methods for providing a purified population of neural stem cells include, but are not limited to, FACS, magnetic sorting, serial passaging, cloning, and affinity chromatography. These methods may be used to purify cells from a tissue explant or a mixed population of cells grown that has been grown in culture. Suitable purified cells for practicing the invention, and the methods for making them, are disclosed in the following publications, the disclosures of which are incorporated by reference: U.S. Pat. Nos. 5,196,315, 5,766,948, 5,968,829, 6,468,794, 6,638,763, 6,680,198, 6,767,738, 6,852,532, 6,897,061 and 7,037,719; and U.S. Patent Publication Nos. 20020086422, 20040253719, 20050003531, 20050125848, 20050142569 and 20060099192.

The invention may also be practiced with mesenchymal stem cells. That is, the invention's combination of environmental factors and cell culture conditions can be used to produce a population of mesenchymal stem cells having enhanced proliferation and enhanced differentiation potential. As noted above, "enhanced," when used to refer to a stem cell's proliferation, means any measurable increase in the stem cell's mitotic cell division rate. When used to refer to a stem cell's differentiation potential, "enhanced" means retaining, or inhibiting the loss of, a stem cell's differentiation potential as the stem cell is expanded and passaged in culture.

Mesenchymal stem cells for use with the invention may be derived from any human or non-human tissue that provides stem cells capable of being expanded according to the methods disclosed herein. Suitable tissue sources include prenatal sources, postnatal sources, and combinations thereof. Tissues for deriving a suitable source of mesenchymal stem cells include, but are not limited to, bone marrow, blood (peripheral blood), dermis, periosteum, synovium, peripheral blood, skin, hair root, muscle, uterine endometrium, adipose, placenta, menstrual discharge, chorionic villus, amniotic fluid and umbilical cord blood. Mesechymal stem cells may be derived from these sources individually, or the sources may be combined (before or after enrichment) to produce a mixed population of mesenchymal stem cells from different tissue sources.

Mesenchymal stem cell compositions for use with the invention may comprise purified or non-purified mesenchymal stem cells. Mesenchymal stem cells for use with the invention include those disclosed in the following references, the disclosures of which are incorporated herein by reference: U.S. Pat. Nos. 5,215,927; 5,225,353; 5,262,334; 5,240,856; 5,486,359; 5,759,793; 5,827,735; 5,811,094; 5,736,396; 5,837,539; 5,837,670; 5,827,740; 6,087,113; 6,387,367; 7,060,494; Jaiswal, N., et al., J. Cell Biochem. (1997) 64(2): 295 312; Cassiede P., et al., J. Bone Miner. Res. (1996) 11(9): 1264 1273; Johnstone, B., et al., (1998) 238(1): 265 272; Yoo, et al., J. Bone Joint Sure. Am. (1998) 80(12): 1745 1757; Gronthos, S., Blood (1994) 84(12): 416-44173; Basch, et al., J. Immunol. Methods (1983) 56: 269; Wysocki and Sato, Proc. Natl. Acad. Sci. (USA) (1978) 75: 2844; and Makino, S., et al., J. Clin. Invest. (1999) 103(5): 697 705.

The invention can be practiced using any culture conditions suitable for expanding a population of stem cells as disclosed herein. That is, the invention can be practiced using any cell culture conditions that, when combined with an environmental factor(s) as disclosed herein, produce a population of stem cells having enhanced proliferation, differentiation, engraftment and/or in vivo migration characteristics. As used herein, the phrase "cell culture conditions" includes, but is not limited to, medium formulations, cell culture (e.g. incubator) temperature, cell seeding density, number of passages permitted before the stem cells are harvested for use, maximum cell density (i.e. the maximum density of stem cells that is permitted before the cells are passaged), and combinations thereof. One skilled in the art will appreciate that suitable cell culture conditions will vary with the type of stem cells being cultured and the level of differentiation potential desired.

In some embodiments of the invention, stem cells are grown under conditions that incorporate the use of a culture media that comprises serum. The invention may be practiced with serum from any mammal including, but not limited to, human, bovine, goat, pig, horse, rabbit, rat, and combinations thereof. The amount of serum used may vary according to the intended use of the stem cells being cultured. In some embodiments of the invention, the stem cells are grown in media comprising less than about 5% serum. Some embodiments of the invention culture stem cells in medium containing between about 0.1% and 0.2% serum.

In a non-limiting embodiment of the invention, human bone marrow is used for the production of oxygen modulated mesenchymal stem cells (OM-MSC). A human bone marrow aspirate is collected from a suitable donor and used to prepare a primary cell culture. The primary cell culture is expanded in culture medium. In some aspects, the culture medium may comprise serum (e.g. between about 0.05 and 2% fetal bovine serum). The primary culture is expanded in culture under low oxygen conditions of between about 0.5 and 2% oxygen. The mesenchymal stem cells may be expanded under low oxygen beginning with the primary culture from bone marrow aspirate. In other aspects, the mesenchymal stem cells are expanded under such low oxygen conditions after passaging of the cells, such as for example, after the first, second, third or subsequent passage.

Stem Cell Factors

The invention further contemplates the production and use of stem cell factors for the treatment of medical conditions, alone or in combination with stem cells (e.g. OM-MSC and/or OM-NSC). As used herein, the term "stem cell factor" refers to any biologically active substance that is produced through the metabolic activity of a stem cell. Such substances include, but are not limited to, cytokines, chemokines, peptides, proteins, amino acids, polynucleotides (i.e. RNA or DNA), and combinations thereof. The stem cell factors of the invention have the ability to impart a therapeutic effect when administered according to the methods of the invention disclosed herein, as well as the ability to affect the proliferation, differentiation, engraftment and migration of stem cells, either in vitro or in vivo.

The stem cell factors of the invention may be derived from a number of sources including cultured medium (e.g. from stem cells), stem cell homogenates, or preparations of lyophilized stem cells. Such stem cells include, but are not limited to, mesenchymal stem cells and neural stem cells. In some aspects of the invention, such stem cell factors are obtained from oxygen modulated stem cells, including OM-MSC and OM-NSC. Factors that are derived from OM-MSC, are referred to as oxygen modulated mesenchymal stem cell factors, or "OM-MSCF.". Similarly, stem cell factors derived from OM-NSC may be referred to as oxygen modulated neural stem cell factors or "OM-NSCF."

In non-limiting embodiments of the invention, stem cell factors are produced by obtaining a population of stem cells, and culturing the stem cells under in vitro conditions that incorporate contacting the stem cells with at least one environmental factor, such as culturing the stem cells under reduced oxygen tension, for example. Stem cell factors produced by the stem cells during culture may then be collected by methods readily available in the art. For example, stem cell factors may be obtained from conditioned culture medium produced from the stem cells, or by using the stem cells to create a stem cell lysate. The invention contemplates factors produced from OM-MSC as well as OM-NSC. The invention further contemplates culturing stem cells for the production of stem cell factors in culture medium that is serum free, or in culture medium that comprises serum.

Utility

In some aspects, the invention is used to accelerate the manufacture of stem cells. Thus, the invention decreases the amount of time that is required to obtain a desired number of stem cells. The invention also improves the yield of stem cell manufacture by enabling the stem cells to undergo an increased number of cell passages, while retaining a desired level of differentiation potential.

In some aspects, the invention is used to modulate (i.e. increase or enhance) the therapeutic potential of stem cells. In such embodiments, a stem cell having a first therapeutic potential is grown under suitable conditions and exposed to at least one environmental factor to produce a stem cell having a second therapeutic potential, the second therapeutic potential being greater than the first therapeutic potential. As used herein, a stem cell is considered to have greater therapeutic potential if the stem cell has an increased proliferation rate, increased in vivo migratory ability, increased differentiation potential and/or increased terminal cell activity (i.e. function), relative to a control cell that was not grown under the method of the invention. An increase in stem activity may be observed through an increase in the stem cell's in vivo migration, proliferation and/or engraftment characteristics.

In other aspects, the invention is used to enhance the in vivo migration and/or engraftment potential of a stem cell. When used in reference to "in vivo migration" or "migration," the term "enhance" means that the invention produces a measurable increase in the speed and/or distance that an implanted (e.g. transplanted) stem cell can migrate in vivo, compared to a control stem cell that has not been treated (e.g. cultured) according to the method of the invention. When used in reference to "in vivo engraftment" or "engraftment," the term "enhance" means that the invention produces a measurable increase in the ability of the stem cell to be accepted and nourished by the body of a subject and assume the function of the cells that are in contact with the implanted stem cell.

The invention also provides stem cells and stem cell factors for therapeutic use. In some embodiments, the invention produces stem cells (e.g. neural stem cells) for use in a variety of central nervous system disorders. As used herein, the term "central nervous system disorder," or "CNS disorder," refers to a condition or injury that impairs the normal function of the mammalian central nervous system, such as, for example, neurodegenerative disorders, traumatic injuries (to the brain or spinal cord) and CNS dysfunctions. Neurodegenerative disorders are generally associated with a prolonged deterioration of CNS neural tissue including, but not limited to, Alzheimer's disease, Parkinson's disease, multiple sclerosis (MS), Huntington's disease, amyotrophic lateral sclerosis, cerebral palsy, Gaucher's disease, Tay-Sachs disease, Niemann Pick's disease, sphingomyelin lipidoses, and brain tumors. CNS disorders further include traumatic injuries, such as for example, hemorrhagic stroke, ischemic stroke, and mechanical injuries to the brain and spinal cord. The phrase "CNS disorder" further includes dysfunctions such as, for example, depression, epilepsy, and schizophrenia.

In some aspects, the invention's stem cell compositions are made by suspending an appropriate amount of cells in a pharmaceutically acceptable carrier. As used herein the phrase "pharmaceutically acceptable" means the carrier, or vehicle, does not cause an adverse reaction when administered to a mammal. Such carriers are non-toxic and do not create an inflammatory or anergic response in the body. Pharmaceutically acceptable carriers for practicing the invention include any of the well known components useful for immunization such as, for example, culture media and phosphate buffered saline. Additional physiologically acceptable carriers and their formulations are well-known and generally described in, for example, Remington's Pharmaceutical Science (18.sup.th Ed., ed. Gennaro, Mack Publishing Co., Easton, Pa., 1990) and the Handbook of Pharmaceutical Excipients (4.sup.th ed., Ed. Rowe et al. Pharmaceutical Press, Washington, D.C.), each of which is incorporated by reference.

One aspect of the invention relates to the concentration of cells that are administered to a subject. In this regard, stem cells and/or stem cell factors, may be administered at any concentration that provides a therapeutic effect when administered according to the methods disclosed herein. Suitable stem cell concentrations range between about $10^4$ to about $10^7$ cells/ml. The concentration of cells used for a particular treatment takes into consideration such factors as viscosity restrictions imposed by the diameter of the needle used for injection, as well as the volume of the compositions that are used for treatment. Stem cells and/or stem cell factors may be administered in a single injection, multiple simultaneous injections or multiple sequential injections at the same or different injection sites.

When the invention is practiced using a composition of oxygen modulated neural stem cells (OM-NSC) and/or oxygen modulated stem cell factors (OM-NSCF), such composition(s) may be administered (e.g. injected) to any site within the neural parenchyma (i.e. any region that is located on the neural side of the blood brain barrier of a subject). Accordingly, the OM-NSC and/or OM-NSCFC may be administered to or near the brain, to or the near spinal cord, and combinations thereof.

In some embodiments of the invention, a composition of OM-NSC and/or OM-NSCFC is administered to the subject intrathecally. As used herein, the term "intrathecal administration," or "intrathecally," is intended to include delivering a neural stem cell composition directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, and U.S. Pat. No. 7,011,827, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of the OM-NSC and/or OM-NSCFC composition to any of the above mentioned sites can be achieved by direct injection, or deposition, of the neural stem cell composition. The injection, or deposition, can be, for example, in the form of a bolus injection or continuous infusion.

Ischemic Stroke

In some aspects, the invention is used to treat ischemic stroke. For example, OM-MSC and/or OM-MSCF can be administered alone or in combination with—OM-NSC and OM-NSCF. In preferred embodiments, OM-MSC and/or OM-MSCF are administered intravenously, and OM-NSC and/or OM-NSCF are administered on the central nervous system side of the blood brain barrier. Administration may also take on other forms including, but not limited to, intra-arterial, intramuscular, intraperitoneal, subcutaneous, intramuscular, intraabdominal, intraocular, retrobulbar and combinations thereof.

In exemplary, non-limiting embodiments, the invention treats ischemic stroke through the use of OM-MSC derived from human bone marrow. In general terms, these embodiments may be practiced by creating a cell suspension from a bone marrow explant collected from a human donor. The cell suspension may then be used to seed a culture medium, containing serum for example, and expanded under reduced oxygen tension for a desired number of passages to produce a population of OM-MSC. An effective amount of OM-MSC may then be suspended in a pharmaceutical carrier and administered intravenously to a subject that has experienced an ischemic stroke. In similar embodiments, OM-MSCF are substituted for, or combined with, OM-MSC.

Although specific uses for the invention may be called out here, one skilled in the art will appreciate that the invention lends itself to any utility that benefits from the enhancement of stem cell proliferation and/or differentiation.

EXAMPLE 1

Tissue Collection and Cell Cultures

Human neural stem cells were collected from 8-10 week-old fetal brain. Brain tissue was freshly dissected and dissociated in Accutase (Sigma Aldrich) for 30 min at 37° C. The cells were seeded in different oxygen tensions and condition medium including 20% or 5% oxygen, with serum-free medium, 0.1% serum condition medium, or 0.2% serum condition medium in 100 mm cell culture dish. Neurobasal medium was used for basal medium to maintain NSCs. The components included: Neurobasal (96%; Gibco/Invitrogen, Grand Island, N.Y.); GlutaMAX (1%; Gibco/Invitrogen); Heparin (8 mg/ml; Sigma-Aldrich, St. Louis, Mo.) (26). To this added the following factors were added: basic Fibroblast Growth Factor and Epidermal growth factor (bFGF; 20 ng/ml; EGF; 20 ng/ml; human, recombinant; Chemicon International, Temecula, Calif.) with 0.1% or 0.2% FBS (Hyclone). For routine passaging, TrypLE was used as the dissociating agent (Invitrogen).

Chicken Embryos

Pathogen-free fertilized chicken embryos were obtained from SPEFAS (North franklin, CT) and staged according to Hamburger and Hamilton (H&H) (1951).

Transplantation of Neural Stem Cells in Chicken Embryos.

NSCs were subcultured 72 hr prior to transplantation. Undifferentiated NSCs and differentiated NSCs were collected and a cell sample of $2\times10^5$ cells was prepared for each of the differentiated NSCs and undifferentiated NSCs. The cell samples were injected, i.e. transplanted into telencephalon lateral ventricle of chicken embryos at H&H stage 26. Transplanted chicken embryos were incubated at 37° C. for 6 days. Chicken embryo brains were collected and embedded with OCT Cryo Tech for cryosection.

Immunohistochemistry

Cryosection slides were placed at room temperature for 30 min. Slides were fixed by pre-cooled acetone for 5-10 min at room temperature and treated with 0.3% $H_2O_2$ in 100% methanol for 10 min to quench endogenous peroxidase activity. Slides were washed 3 times with PBS for 5 min each. Chicken brains were incubated with anti-human nestin (1:3000, chemicon international Inc.) and nuclei (1:500, Chemicon International Inc.) for one hour at room temperature. Slides were washed in PBS 3 times, 5 min for each, and exposed to secondary antibodies Alexa fluor 488-conjugated goat anti-mouse IgG (1:400) and Alexa Fluoro 647-conjugated goat anti-rabbit IgG (1:400) for 30 min at room temperature. Slides were washed with PBS 3 times, 5 min each, and counterstained with DAPI for 10 min at room temperature. Slides were washed in PBS 3 times, 5 min for each, and mounted with immunofluorescence mounting media from Sigma-Aldrich.

Results

The results showed in FIGS. 1-5 and table 1.

|  | Serum-free No. 1 | 0.1% Serum No. 2 | 0.2% Serum No. 3 | Serum-free, low oxygen No. 4 | 0.1% serum, low oxygen No. 5 | 0.2% serum, low oxygen No. 6 |
|---|---|---|---|---|---|---|
|  | $6.8 \times 10^5$ cells 14 days | $6.8 \times 10^5$ cells 22 days | $6.8 \times 10^5$ cells 21 days | $6.8 \times 10^5$ cells 9 days | $6.8 \times 10^5$ cells 22 days | $6.8 \times 10^5$ cells 21 days |
|  | $3.4 \times 10^5$ cells 9 days | $6.3 \times 10^6$ cells 11 days | $7.5 \times 10^6$ cells 7 days | $3.4 \times 10^5$ cells 14 days | $6.24 \times 10^6$ cells 8 days | $9.36 \times 10^6$ cells 7 days |
|  | $1.26 \times 10^6$ cells 10 days | $3.64 \times 10^7$ cells 13 days | $2.03 \times 10^7$ cells 5 days | $1.6 \times 10^6$ cells 10 days | $2.88 \times 10^7$ cells 10 days | $4.20 \times 10^7$ cells 5 days |
|  | $2.24 \times 10^6$ cells 8 days | $2.44 \times 10^7$ cells 14 days | $6.86 \times 10^6$ cells 10 days | $6.72 \times 10^6$ cells 9 days | $2.96 \times 10^7$ cells 10 days | $8.52 \times 10^6$ cells 6 days |
|  | $1.06 \times 10^7$ cells 10 days | $1.91 \times 10^7$ cells | $3.16 \times 10^7$ cells 10 days | $3.54 \times 10^7$ cells 8 days | $3.36 \times 10^7$ cells 10 days | $1.92 \times 10^7$ cells 8 days |
|  | $3.56 \times 10^7$ cells 11 days |  | $2.47 \times 10^7$ cells | $2.94 \times 10^7$ cells 8 days | $2.38 \times 10^7$ cells | $2.06 \times 10^7$ cells 8 days |
|  | $6.4 \times 10^6$ cells |  |  | $7.46 \times 10^6$ cells |  | $2.79 \times 10^7$ cells |
| Total | $5.26 \times 10^7$ | $7.99 \times 10^7$ | $8.35 \times 10^7$ | $7.23 \times 10^7$ | $11.58 \times 10^7$ | $11.826 \times 10^7$ |
| Passage | 6 | 4 | 5 | 6 | 5 | 6 |

EXPERIMENT 2

Cell Transplantation to Mammalian Host

The objectives of this study were as follows: 1) to investigate whether intravenous treatment with human adult bone marrow stem cells (HBMSC) alone or in combination with intrathecal treatment with human fetal neural stem cells (HFNSC) 1 day after occlusion provides sensory-motor and cognitive recovery and affect infarct volume in spontaneously hypertensive rats (SHR) subjected to 60 min middle cerebral artery occlusion (tMCAO), 2) to compare the functional recovery following intravenous injections of HBMSC expanded under normal and low O2 tissue culture conditions (HBMSC-LO2).

Seven and 28-point Neuroscore tests were performed to study sensory-motor deficits and general condition on days 1, 3, 7, 14, 21, 28, 35 and 42 post-ischemia. Cylinder test was performed on days 7, 21 and 35 post-ischemia. Cognitive deficits were evaluated by Morris water maze test on days 28-29 post-stroke. Skilled paw function was tested with Montoya's staircase test (pellet reaching and eating) on days 35-39 post-ischemia. Infarct volume and incidence of hemorrhage was evaluated by ex vivo MRI at day 42. After ex vivo MRI, the brains were cryoprotected, frozen on liquid nitrogen and stored at −80° C. for possible further analysis.

Animals were grouped as follows:
Group 1: 15 rats treated with Vehicle, (PBS, 2 ml/kg, i.v.) at 24 hours post-occlusion
Group 2: 15 rats treated with Vehicle, (PBS, 150 µl/kg, i.t.) at 24 hours post-occlusion
Group 3: 15 rats treated with Vehicle, (PBS, 2 ml/150 µl per kg, i.v./i.t.) at 24 hours post-occlusion
Group 4: 15 rats treated with HBMSC $2\times10^6$ cells, 2 ml/kg, i.v.) at 24 hours post-occlusion
Group 5: 15 rats treated with HBMSC-LO2 $2\times10^6$ cells, 2 ml/kg, i.v.) at 24 hours post-occlusion
Group 6: 15 rats treated with serum HFNSC-LO2 $2\times10^6$ cells, 150 µl/kg, i.t.) at 24 hours post-occlusion
Group 7: 15 rats treated with HBMSC-LO2 $2\times10^6$ cells, 2 ml/kg, i.v.) combined with serum HFNSC-LO2 $2\times10^6$ cells, 150 µl/kg, i.t.) at 24 hours post-occlusion
Group 8: 15 naïve rats as controls for behavioral testing Transient MCAO Transient focal cerebral ischemia was produced by MCA occlusion in male SHR rats according to Koizumi with modifications (Koizumi et al. Jpn. J. Stroke 8:1-8, 1986). The rats were anesthetized with 5% isoflurane (in 70% N20 and 30% O2; flow 300 mL/min). During the operation the concentration of anesthetic is reduced to 1.0-1.5%. The rectal temperature is maintained at 37.0±1.5° C. with a homeothermic blanket system. After midline skin incision, the right common carotid artery (CCA) was exposed, and the external carotid artery (ECA) was ligated distal from the carotid bifurcation. A 0.25-mm diameter monofilament nylon thread, with tip blunted, was inserted 22-23 mm into the internal carotid artery (ICA) up to the origin of MCA. After 60 min of ischemia, the MCA blood flow was restored by removal of the thread. The wound is closed, disinfected, and the animals are allowed to recover from anesthesia. The rats were carefully monitored for possible post-surgical complications after the tMCAO. The rats were fed with standard laboratory diet suspended in tap water on days 0-7 after the tMCAO. To prevent dehydration all rats were given an i.p. injection of saline (4 ml per rat) once-a-day for 7 days.

Animals expressing 0-lesion (no detectable infarct) were excluded from the data and analysis.

HBMSC/HFNSC Storage and Preparation for the Study

HBMSC and HFNSC were delivered to Cerebricon by the sponsor as a frozen stock suspension and with instructions how to prepare the cells/solutions for i.v./i.t. injection. The cell suspensions were made fresh each day and stored at room temperature (RT) when not in use. Vehicle was provided by the sponsor. Both HFNSC and HBMSC were tested for the expression of appropriate stem cell markers and for the ability to differentiate into various mature cell types.

Mesenchymal Stem Cells (HBMSC)

MSC were derived from the bone marrow of 24 years old healthy woman. The mononuclear cells were isolated from fresh specimen using Histopague and seeded into Petri dishes. The cells were expanded in DMEM/F12 medium containing FGF-2 and 10% fetal bovine serum (FBS). The cells were tested for human pathogens and further expanded up to passage 5. The expanded cells were harvested and frozen at $15\times10^6$ cells per vial in the freezing medium containing 10% DMSO and 10% FBS using controlled rate freezer. The frozen cells were stored in liquid nitrogen until shipment. The cells were shipped to Cerebricon on dry ice.

Low oxygen grown MSCs were expanded under 5% oxygen condition beginning from passage 2.

Neural Stem Cells (HFNSC)

Neural stem cells were derived from the forebrain of an eight week old human fetus. The cells were isolated by mechanical digestion and plated into Petri dishes. The cells were expanded under 5% oxygen condition in neural basal medium containing FGF-2, EGF, and 0.1% Fetal Clone II serum. The cells were tested for human pathogens and further expanded up to passage 4. The expanded cells were harvested and frozen at $15\times10^6$ cells per vial in the serum-free freezing medium containing 10% DMSO (Cryostor 10) using controlled rate freezer. The frozen cells were stored in liquid nitrogen until shipment. The cells were shipped to Cerebricon on dry ice.

HBMSC (Regular and Low $O_2$) Processing for Infusion

A sterile 50 mL centrifuge tube was placed under the hood and pre-opened. Six (6) vials (each containing $15\times10^6$ cells in 1 mL freezing medium) of frozen cells were thawed in 37° C. water bath. Vials were kept in the bath until small ice crystals (~2-3 mm) were seen. Contents of the vials was transferred into the 50 mL centrifuge tube after which 6 mL of pre-warmed (37° C.) fresh $Ca^{2+}$-free Hank's balanced salt solution (HBSS) was slowly added and the cell suspension was gently mixed. While adding, the tube was gently shaken to ensure homogenous cell suspension. Added further 28 mL fresh HBSS and mixed the contents of the tube carefully without vortexin. After mixing HBMSCs were centrifuged at 450 g for 5 min at RT. Supernatant was discarded and the pellet was re-suspended in 20 mL of fresh HBSS. Cell viability was determined with Trypan blue and hemocytometer. Dilutions 1:2 and 1:4 from the cell suspension were used for evaluation of viability. Before applying cells to the chamber, suspension was mixed carefully. Altogether 3 fields (1×1 mm) were counted and averaged. Optimal count was 20-40 cells/mm$^2$.

The number of viable cells in the mixture was:

$$\left( \frac{\frac{(\text{Number of cells counted})}{(\text{Proportion of chamber counted})}}{(\text{Volume of chamber})} \right) \left( \frac{(\text{Volume of sample dilution})}{\left( \begin{array}{c} \text{Volume of original mixture} \\ \text{in the sample} \end{array} \right)} \right)$$

After cell viability assay, 30 mL HBSS was added to cell suspension after which HBMSCs were centrifuged at 450 g for 5 min at RT. After supernatant removal, cells were re-suspended in $Ca^{2+}$-free 0.01 M PBS to obtain desired $2.0\times10^6$ cells/0.5 ml.

HFNSC Processing for Infusion

A sterile 50 mL centrifuge tube was placed under the hood and pre-opened. Six (6) vials (each containing $15\times10^6$ cells in 1 mL freezing medium) of frozen cells were thawed in 37° C. water bath. Vials were kept in the bath until small ice crystals (~2-3 mm) were seen. Contents of the vials was transferred into the 50 mL centrifuge tube after which 6 mL of pre-warmed (37° C.) fresh $Ca^{2+}$-free Hank's balanced salt solution (HBSS) was added as described above. Added further 28 mL of fresh HBSS and mixed the contents of the tube carefully without vortexin. Determined cell viability as described for HBMSCs. HFNSCs were centrifuged at 130 g for 5 min at RT and supernatant discarded. Cells were re-suspended in $Ca^{2+}$-free 0.01 M PBS to obtain $2.0\times10^6$ cells/50 µL. Homogenous suspension was obtained by slowly mixing cell suspension with a 1000 μL pipette with suitable pipette tip 20-25 times.

Cell Delivery

Twenty-four hours after occlusion the rats were shortly anesthetized by isoflurane and HBMSC and/or HFNSC or vehicle was infused either into femoral vein or intrathecal space.

For intrathecal delivery of HFNSCs, an anesthetized rat was subjected to laminectomy at L-3 level and stereotactical infusion of cells was performed. Briefly, rat was anesthetized, placed in a stereotactic apparatus skin and area surrounding injection site was shaved and disinfected prior surgical laminectomy. After laminectomy and dura being exposed, a 50 μl gas tight syringe containing the HFNSCs was connected to microlitre infusion pump (TSE Systems Germany). The needle (26 G) was guided into the intrathecal space by using stereotactic apparatus. Following needle penetration into intrathecal space CSF was allowed to leak (~20 μl) through the dura opening before starting cell infusion. Vehicle or HFNSCs were infused for 10 min (5 μL/min for 10 min, totaling 50 μL, containing $2.0 \times 10^6$ HFNSCs). After 10 min stabilization period, the needle was carefully withdrawn from intrathecal space. Immediately after needle withdraw, the opening of the dura was sealed with tissue sealant adhesive (Tisseel® Duo Quick, Baxter). Muscles and connective tissue was then sutured in layers before closing the wound. After procedure, rats were placed in a clean recovery cage, after which they were returned to the homecage.

Body Weight

The body weight of each animal was measured before the tMCAO and at days 1, 3, 7, 21, 28, 35 and 42.

Behavioral Testing

A 28-point neuroscore test was used to assess post-ischemic motor and behavioral deficits. The neurological test was conducted by a blinded investigator at: pre-MCAO (baseline) and 1, 3, 7, 14, 21, 28, 35 and 42 d after tMCAO.

The following parameters were analyzed:
Paw placement (max. score 4)
Righting reflex (max. score 1)
Behavior on a horizontal bar (max. score 3)
Behavior on an inclined platform (max. score 3)
Contralateral rotation (max. score 2)
Visual forepaw reaching (max. score 2)
Circling (max. score 4)
Contralateral reflex (max. score 1)
Grip strength (max. score 2)
Motility (max. score 3)
General condition (max. score 3)
The maximum score for a normal rat was 28 points.

A seven-point neuroscore test was used to assess post-ischemic motor and behavioral deficits (modified from Zausinger et al., 2000. Brain Res. 863:94-105,). The neurological test was conducted by blinded investigator at: pre-MCAO (baseline) and 1, 3, 7, 14, 21, 28, 35 and 42 d after tMCAO.

Grade 6: Normal extension of both forelimbs towards the floor when lifted gently by the tail
Grade 5: Consistent flexion of the forelimb contralateral to the injured hemisphere, varying from mild wrist flexion and shoulder adduction to severe posturing with full flexion of wrist, elbow, and adduction with internal rotation of the shoulder.
Grade 4: Dysfunctional rats with a consistently reduced resistance to lateral push towards the paretic side.
Grade 3: Rats circling towards the paretic side if pulled and lifted by the tail.
Grade 2: Rats circling towards the paretic side if pulled by the tail.
Grade 1: Rats circling spontaneously towards the paretic side.
Grade 0: Rats with no spontaneous motion The cylinder test (modified from Schallert and Tillerson in Innovative models of CNS disease: from molecule to therapy. Clifton, N.J., Humana, 1999) was used to quantify the forelimb use asymmetry, while the animal was rearing against the wall of the home cage. The test was performed on days 7, 21, and 35 after tMCAO. The rats were monitored as they move freely in their home cage. Contacts made by each forepaw with the cage wall while rearing were scored by a blinded observer. A total of 15-20 contacts were recorded for each animal, and the number of impaired (left) and non-impaired forelimb contacts as percentage of total contacts was calculated.

Cognitive testing was conducted using the water maze task originally designed by Morris et al (J Neurosci Methods. 1984; 11: 47-60). On day 28 post-stroke, the rats were given a series of 5 trials, 1 hour apart in a large dark-colored tank (200 cm in diameter) filled with clear water at a temperature of $25.0 \pm 1.5°$ C. A submerged platform (square platform: $10 \times 10$ cm; 1.5 cm below water surface) was placed in the northwest (NW) quadrant of the pool. The release point was always the southern end of the pool. The rats were lowered into the pool facing the wall and then released. Each rat was given a maximum of 90 seconds to find the submerged platform. If it did not find the platform within that time, the rat was physically guided onto it. After remaining on the platform for 20 seconds, the rat was removed from the pool and placed in a dry cage. One hour later, each rat was given the second trial, using the same release position and platform position, to measure retention of platform location. This process was repeated a total of 5 times for each rat, each trial 1 hour apart. These 5 trials were then followed by a retention trial 24 hours later.

The swim paths of the rats were recorded with a computer-interfaced camera tracking system and the data analyzed using HVS Image software. For trials 1-5 and retention trial 6 the following parameters were analyzed: 1) time to find the hidden platform (latency), 2) length of path to the hidden platform (these two parameters measure animals' ability to learn and remember the exact location of the platform), 3) swim speed (to assess rats' physical ability to swim), 4) thigmotaxis, "wall hugging" defined as the percentage of swim path limited to outer annulus (swimming in the outermost 15 cm of the pool rather than searching for the hidden platform).

The Montoya's staircase test measures independent forelimb reaching and grasping ability (general and fine coordination and motorics). The test consists of a 15-min trial per day for 5 days on days 35-39 post-tMCAO. The rat was put in a staircase apparatus, where it laid on a central platform reaching for the pellets from staircase on both sides. The staircase has 6 steps baited with a sucrose-flavored pellet (45 mg, Bioserv, UK). The number of pellets reached but dropped (=reached), as well as the successfully retrieved ones (=eaten), was calculated. All rats are food deprived (to 85% of free body weight) 2 days before testing. Rats were tested once-a-day for 5 days.

Brain Processing and Ex Vivo Imaging of Infarct Volume and Incidence of Hemorrhage by T2- and T2*-MRI At endpoint, day 42, the rats were deeply anesthetized with pentobarbital (60 mg/kg Mebunat, Orion Pharma, Finland) and perfused transcardially with heparinized (2.5 IU/ml) saline followed by 4% formaldehyde in 0.1 M PB (phosphate buffer). Thereafter the brains were immersed in 4% formaldehyde in 0.1 M PB for 24 hours before rinsed with PBS. The brain was embedded in perfluoropolyether (FOMBLIN).

T2 and T2*-weighted MRI was performed with the use of a Varian DirectDrive™ console interfaced to a Varian 7.0T horizontal magnet equipped with actively shielded gradient coils. A half-volume coil, driven in quadrature mode, was used for signal transmission and reception. For determination of infarct volume, T2-weighted multislice (12-14 continuous slices) images were acquired using double spin-echo sequence with adiabatic refocusing pulses TR=3 s, TE=80 ms, matrix size of 256×128, FOV of 35*35 mm$^2$, and a slice thickness of 1 mm.

For detection of the hemorrhage, T2* weighted images were obtained using standard gradient echo imaging sequence from the same slices with identical resolution and TR=700 ms, TE=15 ms, flip angle ~50 degree. T2 and T2* weighted images were analyzed for infarct volumes and presence of hemorrhage, respectively, using in-house written software.

After ex vivo imaging the brains were washed with PBS and cut into two 6-mm-thick coronal brain blocks (striatal and hippocampal block) in a brain tissue precision slicer. After cryoprotection in 30% sucrose for 2 days at +4° C., the brain blocks were frozen on liquid nitrogen, and stored at −80° C. for possible future histological and immunohistochemical analysis.

Statistical Analysis

All values are presented as mean±standard deviation (SD) or standard error of mean (SEM), and differences are considered to be statistically significant at the $P<0.05$ level. Statistical analysis was performed using StatsDirect statistical software. Differences between group means were analyzed by using 1-way-ANOVA followed by Dunnet's test (comparison to the control (=vehicle) group). Within group comparison to the baseline was done by two-way ANOVA followed by Dunnet's test. Non-parametric data was analyzed with Kruskal-Wallis ANOVA or Friedman ANOVA, respectively. The animals that expressed no infarct at all (0-infarcts) were excluded from the study.

Results

The Seven Point Neuroscore demonstrates the efficacy of the HBMSC, HBMSC-LO2, HFNSC-LO2, HBMSC-LO2 and HBMSC-LO2/HFNSC-LO2 cell compositions.

We claim:

1. A method for treating an ischemic stroke in a patient comprising:
    a. intrathecally administering to the patient a therapeutic amount of neural stem cells; and
    b. intravenously administering to the patient a therapeutically effective amount of mesenchymal stem cells;
    wherein the neural stem cells have been exposed to reduced oxygen tension and the mesenchymal stem cells have been grown under reduced oxygen tension for a plurality of passages.

2. The method of claim 1, wherein the neural stem cells and the mesenchymal stem cells are cultured in a culture medium comprising serum.

3. The method of claim 1, wherein the mesenchymal stem cells are grown under reduced oxygen tension for four passages.

* * * * *